(12) United States Patent
Rovegno (10) Patent No.: US 8,197,397 B2
(45) Date of Patent: *Jun. 12, 2012

(54) METROLOGY DEVICE FOR VIDEOENDOSCOPIC PROBE

(75) Inventor: Jean Rovegno, La Ciotat (FR)

(73) Assignee: Tokendo, La Ciotat (FR)

( * ) Notice: Subject to any disclaimer, the term of this patent is extended or adjusted under 35 U.S.C. 154(b) by 642 days.

This patent is subject to a terminal disclaimer.

(21) Appl. No.: 12/389,169

(22) Filed: Feb. 19, 2009

(65) Prior Publication Data

US 2009/0160935 A1    Jun. 25, 2009

Related U.S. Application Data

(63) Continuation of application No. 11/010,127, filed on Dec. 10, 2004, now Pat. No. 7,507,201.

(30) Foreign Application Priority Data

| Dec. 11, 2003 | (FR) | .................................... 03 14526 |
| Dec. 19, 2003 | (FR) | .................................... 03 015079 |
| Jan. 28, 2004 | (FR) | .................................... 04 00808 |

(51) Int. Cl.
*A61B 1/00* (2006.01)
*A61B 1/04* (2006.01)
*A61B 1/06* (2006.01)
*H04N 13/02* (2006.01)
*H04N 15/00* (2006.01)

(52) U.S. Cl. ........................ 600/111; 600/160; 348/49

(58) Field of Classification Search .................. 600/111, 600/166, 175; 348/45, 49; 382/154, 286, 382/291, 294
See application file for complete search history.

(56) References Cited

U.S. PATENT DOCUMENTS

| 4,727,859 | A  | 3/1988  | Lia |
| 4,873,572 | A  | 10/1989 | Miyazaki et al. |
| 5,522,789 | A  | 6/1996  | Takahashi |
| 6,104,426 | A  | 8/2000  | Street |
| 6,361,491 | B1 | 3/2002  | Hasegawa et al. |
| 6,839,081 | B1 | 1/2005  | Iijima et al. |
| 6,890,296 | B2 | 5/2005  | Ogawa |
| 6,914,623 | B2 | 7/2005  | Ogawa |
| 6,945,930 | B2 | 9/2005  | Yokota |
| 7,048,685 | B2 | 5/2006  | Sakiyama |
| 7,170,677 | B1 | 1/2007  | Bendall et al. |
| 2002/0161284 | A1 | 10/2002 | Tanaka |
| 2003/0060679 | A1 | 3/2003  | Murata et al. |

FOREIGN PATENT DOCUMENTS

DE    3806190 A1    9/1988

*Primary Examiner* — Philip R Smith
(74) *Attorney, Agent, or Firm* — Robert Iannucci; Seed IP Law Group PLLC (57) ABSTRACT

Image splitting device for videoendoscope, comprising an image splitting optical component to form on the sensitive surface of a video sensor housed in the distal end part of a videoendoscope a single composite image formed from two images of an observed target, viewed from two different angles; the image splitting optical component comprises two sections of identical convergent lenses, integrated into an opaque central element, maintaining the space between the two sections of lenses, each of the two sections of lenses are at least equal to a half-moon so that it is crossed by the optical axes of the lens.

21 Claims, 6 Drawing Sheets

METROLOGY DEVICE FOR VIDEOENDOSCOPIC PROBE

CROSS-REFERENCE TO RELATED APPLICATION

This application is a continuation of U.S. patent application Ser. No. 11/010,127, filed Dec. 10, 2004, now pending, which application is incorporated herein by reference in its entirety.

BACKGROUND OF THE INVENTION

1. Field of the Invention

The invention relates to videoendoscopes equipped with a device for measuring the dimensions of a target located in the observation field of the videoendoscope.

It is particularly, but not exclusively, applicable to industrial endoscopy.

2. Description of the Prior Art

Normally, the term "endoscope" is given to a flexible or rigid probe, designed to be inserted into an obscure cavity and allowing the user to observe through an eyepiece the image of a target located inside the cavity. To this end, an endoscope comprises a lighting device of the target and an optical device providing the user with an image of the target. The optical device comprises a distal lens, an image transportation device that may be rigid and composed of a series of lenses, or flexible composed of a bundle of sorted optical fibers, and a proximal eyepiece in which the user can observe the image of the target. The lighting device normally comprises a bundle of lighting fibers whose distal tip, conveniently directed near the distal lens, lights the target when its proximal tip is connected to a light generator.

The term "videoendoscope" therefore refers to a flexible or rigid probe that allows the user to observe on a video screen the image of a target located inside an obscure cavity. To this end, a videoendoscope comprises a lighting device of the target that is identical to that of an endoscope and an imaging device that provides the user with a video image of the target. The imaging device comprises an optoelectronic device composed, in particular, of an optical device and a CCD (Charge Coupled Device) sensor on the sensitive surface from which the image is formed of the target delivered by said optical device, a video processor electrically connected to the CCD sensor that transforms the electric signal delivered by the CCD sensor into a video signal, a control panel for adjusting the main operating parameters of the video processor, and a video monitor for viewing the video signal delivered by the processor.

The term "videoendoscopic probe" refers to a videoendoscope comprising the following elements:

a distal end part that houses an optoelectronic imaging device including, notably, a lens and a CCD sensor, a flexible inspection tube whose distal end is integrated into the distal end part, a control handle integral with the proximal end of the inspection tube, a flexible umbilical connection cable distal end of which is integrated into the control handle and the proximal end of which is designed to be connected to an external unit that integrates, notably, a light generator and an electric power supply source, a bundle of lighting fibers housed in the umbilical cable, in the control handle, then in the inspection tube and whose distal end, housed in the distal end part, lights the target when its proximal end is connected to a light generator, a video processor electrically connected to the distal end part and whose synchronization is adjusted according to the length of the electric cable connecting it to the distal end part, a video monitor connected to the video processor, and a control panel that allows adjusting the operation of the video processor and possibly the video monitor.

The recently designed videoendoscopic probes can include, among other things, the following elements:

an articulated distal tip deflection that allows modifying the direction of the distal end part of the probe, the control handle that then generally integrates the mechanical or electromechanical command means for activating this tip deflection, interchangeable optical heads that can be adapted to the distal end part of the inspection tube and that allow modifying the optical field open by the videoendoscope and/or the directions of the optical view and light axes of the videoendoscope, and an image freeze, recording, pointing, and processing digital system that can be directly controlled by the control panel of the videoendoscope. Such a system can, among other things, be used for metrology purposes.

Within the scope of inspection of mechanical pieces, it might be desired to add to the viewing function of the videoendoscope a metrology function enabling the user to directly measure the dimensions of certain elements of the observed mechanical piece. The implementation in a videoendoscope of a metrology function is generally performed using the following means:

an optical means that can be integrated into the opto-electronic distal device of the videoendoscope for viewing a parameter whose position in the image delivered by the videoendoscope reflects the true distance separating the distal end of the videoendoscopic probe and the target to be measured, an electronic means connected to the videoendoscope for enabling the operator to point on the video monitor the above-mentioned parameter, as well as the ends of the target to be measured, and for implementing a mathematical algorithm that can deduce from these points the observation distance and the dimensions of the observed target.

The metrology methods that are most commonly used first in traditional endoscopy and then in videoendoscopy are briefly described below.

Direct Measure by Moving the View Axis

This method is only applicable to rigid side view endoscope and consists in pointing using optical means (U.S. Pat. No. 4,702,229) or electronic means (U.S. Pat. No. 4,820,043) the ends of a target by moving lengthwise the endoscope by one mechanical measurable value.

Measure by Optical Crosshairs

This method is also only applicable to rigid endoscopes and only for repetitive measurements performed on identical targets. It consists in optically superimposing on the image of the target an image of a graduated reticule placed on the distal focal plane of the endoscope eyepiece and specific to the mechanical piece forming the target. Endoscopes equipped with such a reticule are generally deviated view endoscopes that include attached devices for focusing, varying the view angle, rotating the view axis around the endoscope axis, and also rotating the reticule. Such endoscopes are described in U.S. Pat. No. 6,333,812 and FR 2 832 516. In document JP11045649, also foreseen is the electronically superimposing on the video image of the target a meshed network specific to the mechanical piece to be measured.

Measure by Moving an Optical Component

This method is applicable to rigid endoscopes the optical device proximal end of which may be integral with an optoelectronic device including notably a lens and a CCD sensor. It consists in visually adjusting an optical parameter by moving lengthwise one of the optical components of the endoscope optical device along a distance which can be directly measured using mechanical, optical or electronic means, and deriving the observation distance and then the dimensions of the target from the distance of this movement. The optical parameter to be adjusted can be the image sharpness that results from moving the proximal adjustment lens (U.S. Pat. No. 6,100,972, WO 96/20389) or the distal lens (U.S. Pat. No. 4,558,691) of a low field depth optical device. This parameter can also be the image magnification (U.S. Pat. No. 6,476,979) resulting from the movement of one of the lenses of an optical device with a variable focal length.

Measure by Comparison

This method can only be used in videoendoscopy and consists in subtracting the unknown dimensions of a target from the known dimensions of a standard target using electronic pointing and calculation tools that allow directly comparing on the video screen of a videoendoscope the image dimensions of the two above-mentioned targets. Thus, in U.S. Pat. No. 4,207,594, the diameter of the object field covered by the videoendoscope distal lens is used as standard target, the target to be measured being located in the object field. In a more realistic manner, documents GB 2 269 453 and IL 156 074 foresee using as a standard target a spot light with invariable dimensions obtained by projecting a collimated light beam on the area in which the target to be measured is located.

Measure by Projecting an Auxiliary Image on the Target

This method, used originally in traditional endoscopy, is for example described in patents DE 2 847 561 and U.S. Pat. No. 4,660,982. It consists in projecting on the target viewed by the endoscope a non-collimated image generated by a mask associated to a lens integrated into the distal end of the lighting device of the endoscope. The observation distance and the dimensions of the target can then be deduced from the position and dimensions, in the image field of the endoscope eyepiece, on the one hand from the image of the target, and on the other, from the image of the auxiliary image. This method is applied in videoendoscopy according to the implementation methods described in U.S. Pat. No. 4,980,763 and U.S. Pat. No. 5,070,401. In parallel, the measurement using a similar method of a target located in the observation field of a video camera connected to a laser projector by applying to the target a non-collimated spot light has been described in patent FR 2 630 539. In these two methods, the use of electronic calculation and pointing tools on the video screen of the images of the target and of the auxiliary image has allowed simplifying the implementation of measurement procedures. Patent DE 3629435 describes another measurement method that can be used both in traditional endoscopy and videoendoscopy and combines a measurement method by comparison (use of a standard target formed by the images of two collimated laser beams parallel to the optical axis) and a measurement method by projecting an auxiliary image (image of a third collimated laser beam inclined with respect to the optical axis.)

Traditional Dual Optical Path Stereo Measure

This method consists in forming on the sensitive surface of the distal CCD sensor of a videoendoscopic probe two images of the target observed under different angles thanks to two distinct distal optical paths. The observation distance and dimensions of the target can therefore be deduced using the electronic pointing and calculation tools of the relative positions and the dimensions on the video screen of the probe of these two images. These two images can be simultaneously generated by two distinct lenses positioned at the distal end of the probe (U.S. Pat. No. 4,873,572, US 2002/0137986, U.S. Pat. No. 6,063,023) or sequentially thanks to the alternating implementation of two pupils integrated into the distal lens of the probe and positioned symmetrically with respect to the optical axis (U.S. Pat. No. 5,222,477).

Measure by Image Splitting

There are also stereo display procedures implemented not in endoscopy, but rather in the stereoscopic television domain. These procedures originally consisted (for example according to U.S. Pat. No. 3,932,699, FR 2 619 664, FR 2 704 951, FR 2 704 951, FR 2 705 006) in associating two homothetic lenticular networks comprising the same number of image splitting unit optical elements, the smallest of the two networks was placed in front of the lens of a video camera, whilst the larger was adhered to the tube of a television receiver connected to said camera. A measurement method, derived from these display procedures is described in U.S. Pat. No. 4,993,380. The simultaneous implementation of LCD type video monitors composed of a pixel matrix and image processing programs that allows managing the signal received by each of these pixels has allowed improving these procedures, on the one hand by finely relating the structure of the reception lenticular network to that of the pixel matrix of the video monitor, and on other hand, by no longer using only one optical image splitting element at the video camera level, and thus improving the optical quality of said element. Thus the French inventor Pierre ALLIO, applicant of a large number of patents in this domain, has presented in the April 2003 issue of the French magazine "Science & Vie" an image splitting optical device designed to be placed in front of the lens of a television camera and comprising:

a proximal optical element with a flat distal face and a proximal face equipped with a concave transversal profile, a distal optical element with a distal face equipped with a convex transversal profile placed perpendicularly with respect to the concave profile of the proximal element and a proximal face in which two parallel and adjacent transversal strips are machined, each presenting an identical concave profile and placed perpendicularly with respect to the concave profile of the proximal element.

As already indicated in patent DE 3 432 583, the implementation of a measuring procedure that uses a discrete image splitting device composed of a simple optical component with a flat distal surface and a projected edge delta-shaped proximal face has been described in patents U.S. Pat. No. 4,411,327 and US 2002/0089583. Designed not to be integrated in a videoendoscopic probe, but rather to be placed in front of the lens of a video camera, this device is designed to measure the observation distance of a target placed in the vicinity of the optical axis of a traditional video camera.

It turns out that the stereo devices that simultaneously form on the CCD sensor two images of a target under two different view angles offers greater accuracy and repetitiveness of measurements. Nevertheless, the three stereo devices described above that allow obtaining such a result present significant, even prohibitive drawbacks as regards to their integration into a very small diameter videoendoscopic probe. Indeed, the integration of two axial view lenses in the axial end of a videoendoscopic probe requires the implementation of very small diameter lenses which prevent the entire sensitive surface of the CCD sensor connected to the lenses to be used. These limitations are not directed at the optimization of the accuracy of the measurement process. Furthermore, the integration into the distal end of a videoendoscopic probe of an image splitting device that have concave rectilinear transversal profiles becomes difficult to perform due to the miniaturization difficulties of such a device. In contrast, the implementation of a discrete image splitting device composed of a prism with a delta shape section does not present any problem in terms of miniaturization. Nonetheless, the optical measuring field of such a prism turns out to be, in principle, less than 15 degrees, a value that is clearly insufficient for an endoscopic measurement system.

The flexibility of use of a videoendoscopic probe supposes the possibility of adapting its distal end to removable and interchangeable observation heads that cover different field and/or view angle values. Obviously, it is preferable that the optical device necessary for implementing a measurement procedure can be also integrated into a removable head, knowing that in this case, the mechanical devices ensuring positioning and unlocking of the removable heads with respect to the CCD sensor of the probe must meet the highest accuracy requirements. In a general manner, the locking devices of a removable head on a distal end of a videoendoscopic probe must meet the following requirements:

continuity of the optical paths and light paths of the videoendoscopic probe and the removable head; this function requiring the simultaneous implementation of a longitudinal lock and a side indexation, prevention of any possibility of accidental unlocking of the removable head, absence of pollution of the CCD sensor due to emitted parasite light beams of the light path of the probe.

The mechanical means implemented to meet these limitations vary according to the optical structure of the probe/removable head pair. More often, as is the case in U.S. Pat. No. 4,727,859, the CCD sensor of the probe is connected in a fixed manner to a distal optical device with a front compactness that is lower than the CCD sensor. The optical device can under these conditions be housed in the distal section of the probe that can therefore have a diameter that is less than the diameter of the probe in order to be able to be encased by the proximal tubular end of the removable heads. This architecture has the advantage of simplifying the locking devices and the disadvantage of having to house in the removable heads optical devices in additional to the one integrated permanently into the probe. On a purely optical point of view, it turns out to be more technically advantageous to house the entire optical system in removable heads that are fixed directly to the CCD sensor integrated into the probe, knowing that the mechanical locking devices will therefore be more delicate to design.

SUMMARY OF THE INVENTION

The object of the invention is to create an image splitting optical device that can be integrated into the distal end of a small diameter videoendoscopic probe, presenting the following advantages:

offering a significant measuring field, allowing the use for these measurements of an important part of the sensitive surface of the CCD sensor, and capacity to be integrated into interchangeable heads with optical axial view or deviated view and that can be connected to the distal end of a videoendoscopic probe, and including a minimum number of optical components so as to present a limited size.

This object is achieved by an image splitting device for a videoendoscope, comprising an image splitting optical component to form on a sensitive surface of a video sensor housed in a distal end part of a videoendoscope a single composite image formed from two images of an observed target, viewed under two different angles.

According to the invention, the image splitting optical component comprises two sections of identical convergent lenses, integral with an opaque central element, maintaining the two sections of lens spaced apart, each of the two sections of lens being at least equal to a half-moon so as to be crossed by the optical axis of the lens.

According to a preferred embodiment of the invention, the image splitting optical component is connected to an opaque mask with two holes forming two diaphragms that are centered respectively on the optical axes of the two lens sections.

According to a preferred embodiment of the invention, the image splitting optical component is obtained by performing a cut according to a circular right section cylinder, centered on the opaque element and whose longitudinal axis is parallel to the optical axes of the lens sections.

According to a preferred embodiment of the invention, the image splitting device further comprises a convergent lens placed in a proximal position with respect to the splitting optical component, the assembly of the splitting optical component and the convergent lens forming a distal lens of a videoendoscope.

Advantageously, the image splitting device further comprises a divergent lens placed in a distal position with respect to the splitting optical component.

According to a preferred embodiment of the invention, the image splitting device further comprises reflection means placed in a distal position, for inserting a deviation of the view angle of the image splitting device.

Advantageously, the image splitting device further comprises a divergent lens placed in a distal position with respect to the reflection means.

According to a preferred embodiment of the invention, the image splitting device is in the form of an optical head comprising fixing means for being fixed in a removable manner on a distal end part of a videoendoscope to form a split image on the sensitive surface of a video sensor housed in the distal end part.

Advantageously, the fixing means are of the finger type designed to cooperate with a groove in the form of a bayonet, and comprise coupling means for ensuring correct alignment of the optical axis of the optical head with the video sensor.

According to a preferred embodiment of the invention, the image splitting device comprises a bundle of lighting fibers having a distal end designed to light a target to be viewed and a proximal end designed to be coupled to the distal end of a bundle of lighting fibers equipping the videoendoscope, the coupling means ensuring a correct alignment of the bundle of lighting fibers with that of the videoendoscope.

Advantageously, the fixing means are formed on a locking tube which is mobile in an axial manner on the optical head between distal and proximal positions, and are brought back to the distal position by resilient return means, the coupling means being of the type male-female and placed in such a way so as to arrive in a coupled position at the end of a locking path of the locking means under the effect of the resilient return means.

The invention also relates to a videoendoscope comprising a distal end part that houses a video sensor. According to the invention, the video sensor is coupled to an image splitting device as described above.

According to a preferred embodiment of the invention, the videoendoscope comprises means for calculating an observation distance of a point of the target from a distance on the display screen on which is displayed the composite image of the target formed on the video sensor, between two image points of the target point, generated by the image splitting device.

According to a preferred embodiment of the invention, the videoendoscope further comprises means for calculating the distance between a first and second point of the target from the respective positions on the display screen on which is displayed the composite image of the target formed on the video sensor of two image points of the first point of the target and of two image points of the second point, generated by the image splitting device.

According to a preferred embodiment of the invention, the videoendoscope further comprises means for applying to a portion of the composite image representing the observed target, a magnifying process, so as to display only one of the two images of the target, composing the composite image.

According to a preferred embodiment of the invention, the videoendoscope further comprises a pair of stereo vision glasses comprising two mini video screens to which are sent respectively the two split images of the target, after having been subjected to a magnification process.

Advantageously, the video sensor is a CCD sensor.

The invention will be more clearly understood and other features and advantages of the invention will emerge from a reading of the following description of preferred embodiment given with reference to the appended drawings.

DETAILED DESCRIPTION OF THE PREFERRED EMBODIMENT

Figure 1:
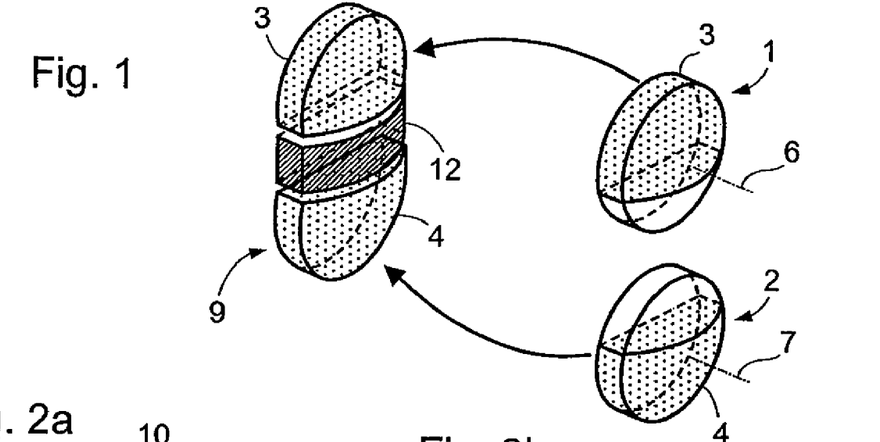
FIG. 1 represents in an exploded perspective view, a part of an image splitting optical component according to the invention.

FIG. 1 schematically represents the structure of an image splitting optical component 10 according to the invention.

The optical component 9 shown on this figure is obtained by bringing together an opaque central element 12 and two identical side sections 3, 4 of lenses 1, 2 larger than a half-lens or half-moon in order to include the optical axes 6, 7 of the lenses 1, 2. Each of these lens sections is obtained by cutting a convergent lens 1, 2, for example according to a cutting plane parallel to the optical axis of the lens, the convergent lens having a flat face and a convex face. The optical component 9 shown in FIG. 1 thus presents two perpendicular symmetry planes, namely, a mediator plane of the central element 13 dividing each of the two lens sections and the central element into two symmetrical parts and a mediator plane of the central element on either side of which the two lens sections are placed symmetrically.

Figure 2A:
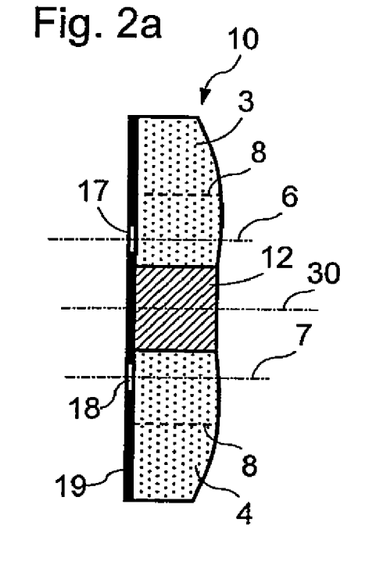
FIGS. 2a and 2b show respectively the longitudinal section and the front view of the structure of the optical component according to the invention, integrating the part represented in FIG. 1.
Figure 2B:
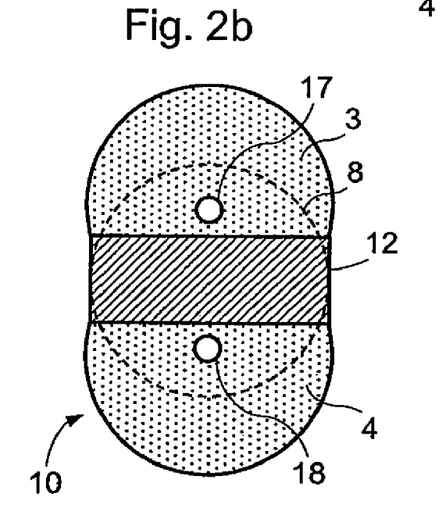

FIGS. 2a and 2b show a front and profile view of an optical component 10 obtained by attaching the optical component 9 represented in FIG. 1 to an optical mask 19 glued to the flat face of the component 9, this mask having two circular holes 17, 18 serving as opening diaphragms which are centered on the optical axes 6, 7 of the two lens sections 3, 4.

Figure 3A:
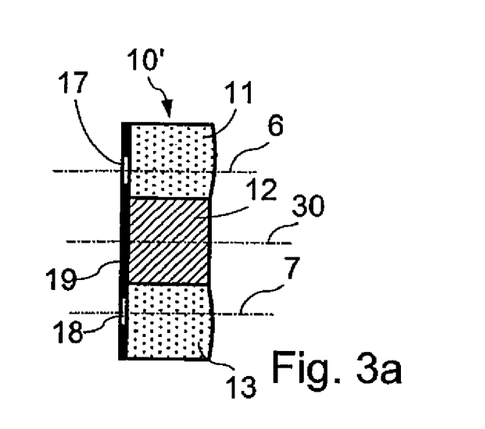
FIGS. 3a and 3b show respectively the longitudinal section and the front view of the structure of a variant of the optical component represented in FIGS. 2a and 2b.
Figure 3B:
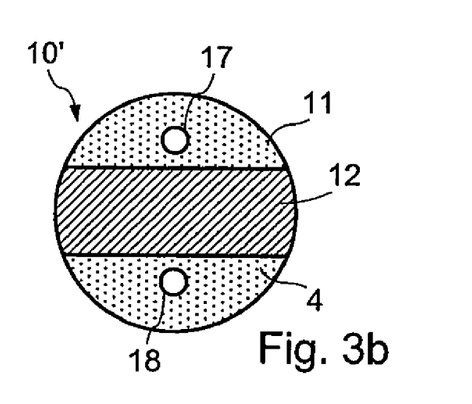

FIGS. 3a and 3b represent a variant 10' of the image splitting optical component according to the invention. The optical component shown in this figure is obtained by cutting the optical component 10 represented in FIGS. 2a and 2b according to a circular right section cylinder 8, centered on the latter and whose longitudinal axis is parallel to the optical axes of the lens sections 3, 4. The component thus obtained has the dimensions of a circular lens.

Figure 4:
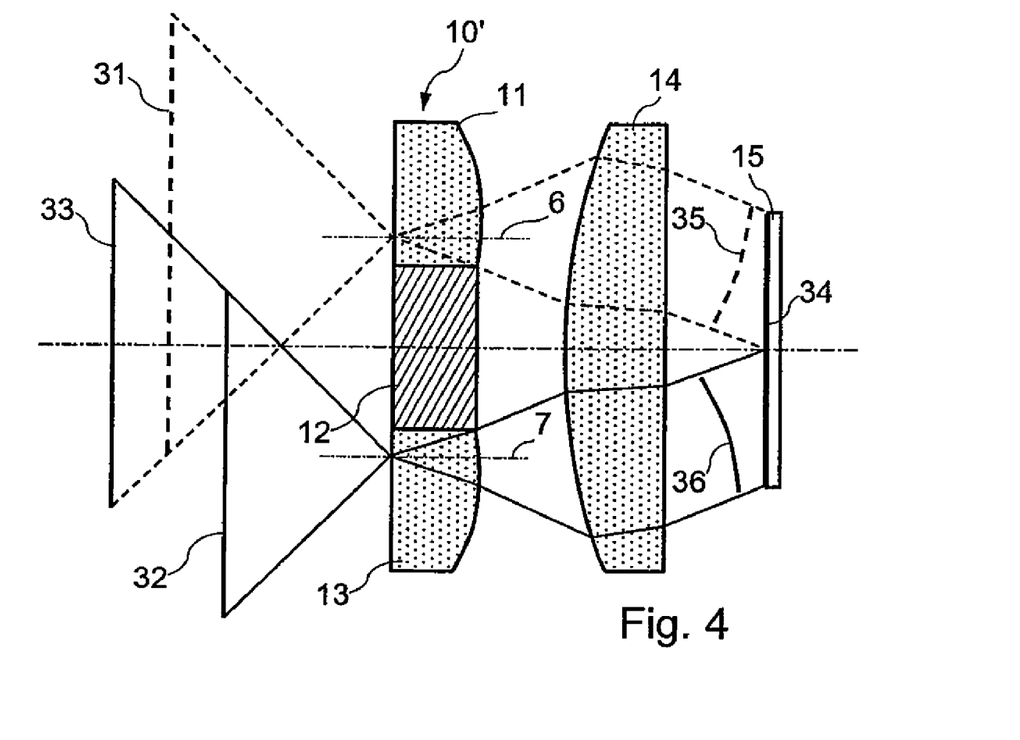
FIG. 4 represents the distribution of the optical fields transmitted by the optical component represented in FIGS. 3a and 3b.

FIG. 4 schematically illustrates the distributions of the optical fields transmitted by the opto-electronic measuring device according to the invention. This device comprises a proximal CCD sensor 15, a converging central lens 14, and the distal image splitting optical component 10 or 10' described in reference to FIG. 2a, 2b or 3a, 3b. In the optical system comprising the side lens section 11 of the distal optical component 10, 10' and the central lens 14, the object field 31 covered by the lens section 11 forms on the proximal CCD sensor 15 an image field 35 that substantially covers half the sensitive surface 34 of the CCD sensor. In the same way, in the optical system comprising the side lens section 13 of the distal optical component 10, 10' and the central lens 14, the object field 32 covered by the lens section 12 forms on the sensitive surface of the CCD sensor an image field 36 that substantially covers the other half of the sensitive surface 34 of the CCD sensor, not covered by the image field 35. The result is that each of the object points located in the object field 33 located in the intersection of the two object fields 31, 32 generates two distinct image points on the sensitive surface of the CCD sensor 15.

It should be noted that the distribution of the image fields 35, 36 into two distinct halves of the sensitive surface of the CCD sensor 15 (and therefore the absence of overlapping of these two images in the center of the sensitive surface of the sensor) is obtained by correctly calculating, on the one hand, the thickness and height of the central opaque element 12, and on the other, the deviation separating the optical axes 6 and 7 of the two side lens sections 11 and 13.

It should be noted that the structure of the opto-electronic distal device with an axial measurement described above arises directly from that of a distal axial view opto-electronic device integrated into the distal end of a traditional videoendoscopic probe. Indeed, such a display device comprises a proximal CCD sensor 15 and a distal lens composed of at least one proximal convergent lens 14 and a distal convergent lens. The transformation of the display device into a measuring device is therefore performed simply by replacing the distal convergent lens with the optical component 10, 10' described with reference to FIG. 2a, 2b or 3a, 3b. Under these conditions, and always by analogy with the distal axial view opto-electronic devices used in traditional videoendoscopy, it should be noted that the distal axial measurement opto-electronic device according to this invention can easily be improved by adding a distal divergent lens that would enlarge the optical fields 31, 32 and therefore also the common measurement optical field 33.

Figure 5:
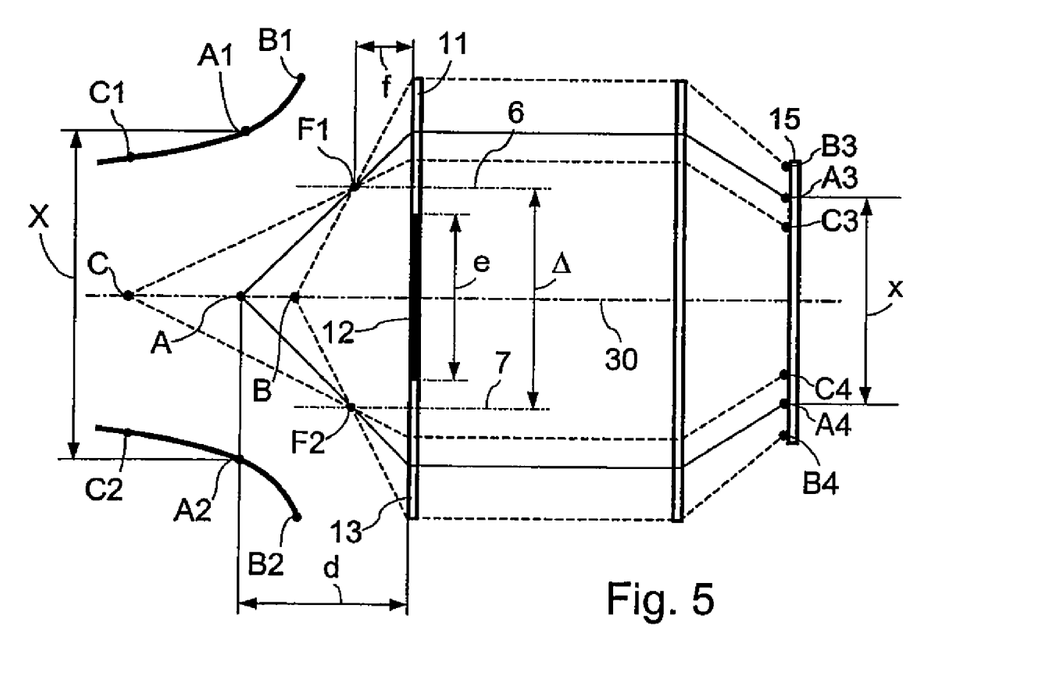
FIG. 5 illustrates the geometric relationship on which is based the algorithm for calculating the distance between a point located in the optical measuring field and the distal end of the optical component represented in FIGS. 3a and 3b.

FIG. 5 schematically illustrates the geometric process implemented in the distal axial measurement opto-electronic device according to the invention. In this process, an object point A located on the optical axis 30 of the measurement field 33 forms a pair of image points A3, A4 on the sensitive surface of the CCD sensor 15. Considering the deviation with respect to the optical axis 30 of the focal point F1 of the distal lens section 11, this lens section generates a virtual image A1 of the object point A, this virtual image having a deviation with respect to the optical axis 30 that depends on the distance d that separates the object point A from the distal end of the measurement opto-electronic device. The recovery of the virtual image A1 by the central lens 14 generates an image point A3 on the sensitive surface of the CCD sensor 15. In the same way, and considering the deviation with respect to the optical axis 30 of the focal point F2 of the distal lens section 13, this lens section generates a virtual image A2 of the object point A. The recovery of the virtual image A2 by the central lens 14 generates an image point A4 on the sensitive surface of the CCD sensor 15. In the same way, an object point B located at a shorter observation distance than that of point A is related to two virtual images B1, B2, then to two image points B3, B4 on the sensitive surface of the CCD sensor 15. An object point C, located at a longer observation distance than that of point A is related to two virtual images C1, C2, and then to two image points C3, C4.

It should be noted that although not indicated on FIG. 4, an object point offset with respect to the optical axis 30 and located in the measurement field 33 in line with the object point A also generates two virtual images whose deviation will be identical to that which separates the two virtual images A1, A2, and forms on the sensitive surface of the CCD sensor 15 two image points whose deviation is identical to that separating the two image points A3, A4.

It can also be noted that the virtual images A1, B1, C1, on the one hand and on the other hand A2, B2, C2 are distributed over two hyperbolic curves that are symmetrical with respect to the optical axis 30. This distribution proves that the accuracy of the observation distance measurement of an object point located in the measurement field 33, measurement resulting in an equivalent measurement of the deviation separating the two virtual images of said object point, will be more accurate for short observation distances (any object point located between A and B, for example) than for longer observation distances (any object point located, for example, between A and C.) Under these conditions, it would be prudent to foresee in the observation distance calculation procedure an alarm that is triggered when the deviation separating the two image points of a same object point, displayed on the video screen of the videoendoscopic probe is less than a default threshold value corresponding to an unacceptable degradation of the observation distance measurement accuracy.

FIG. 5 also illustrates the geometric relation from which the algorithm results, allowing the calculation of the observation distance d that separates an object point A located in the measurement optical field 33, from the distal end of the distal axial measurement opto-electronic device according to the invention. This observation distance is based on the knowledge of the focal distance f of the lens sections 11, 13, on the knowledge of the deviation Δ separating the two optical axes 6, 7 from the lens sections 11, 13, and on the measurement of distance X separating the two virtual images A1, A2. The observation distance d is obtained using the following equation:

$$d = fX/(X-\Delta) \quad (1)$$

In practice, distance X is obtained by measuring the effective deviation separating the two image points displayed on the video screen of the videoendoscopic probe, this deviation being proportional to deviation x separating the two image points A3, A4 formed on the sensitive surface of the CCD sensor 15. Deviation x is itself proportional to deviation X separating the two virtual images A1, A2 of object point A.

The measurement of the real length of a defect (for example, a crack), this measurement type being the first vocation of videoendoscopic probes according to this invention, implements calculation and scaling procedures that will not be described in this description. Practically, such a length measurement indeed requires a previous calculation of the real spatial coordinates of the defect ends. In addition to the observation distances of said ends (distances whose calculation principle has been described above,) such a calculation requires taking into account other parameters that could be obtained either from the structure itself of the videoendoscopic probe (overall enlargement of the system comprising the distal measurement opto-electronic device, the video processor, and the video screen of the probe), or using pointing on the video screen of the image ends of the defect (view angles of the ends of the defect), or using a previous scaling (correction of optical distortions).

Figures 6, 7, 8, 9:
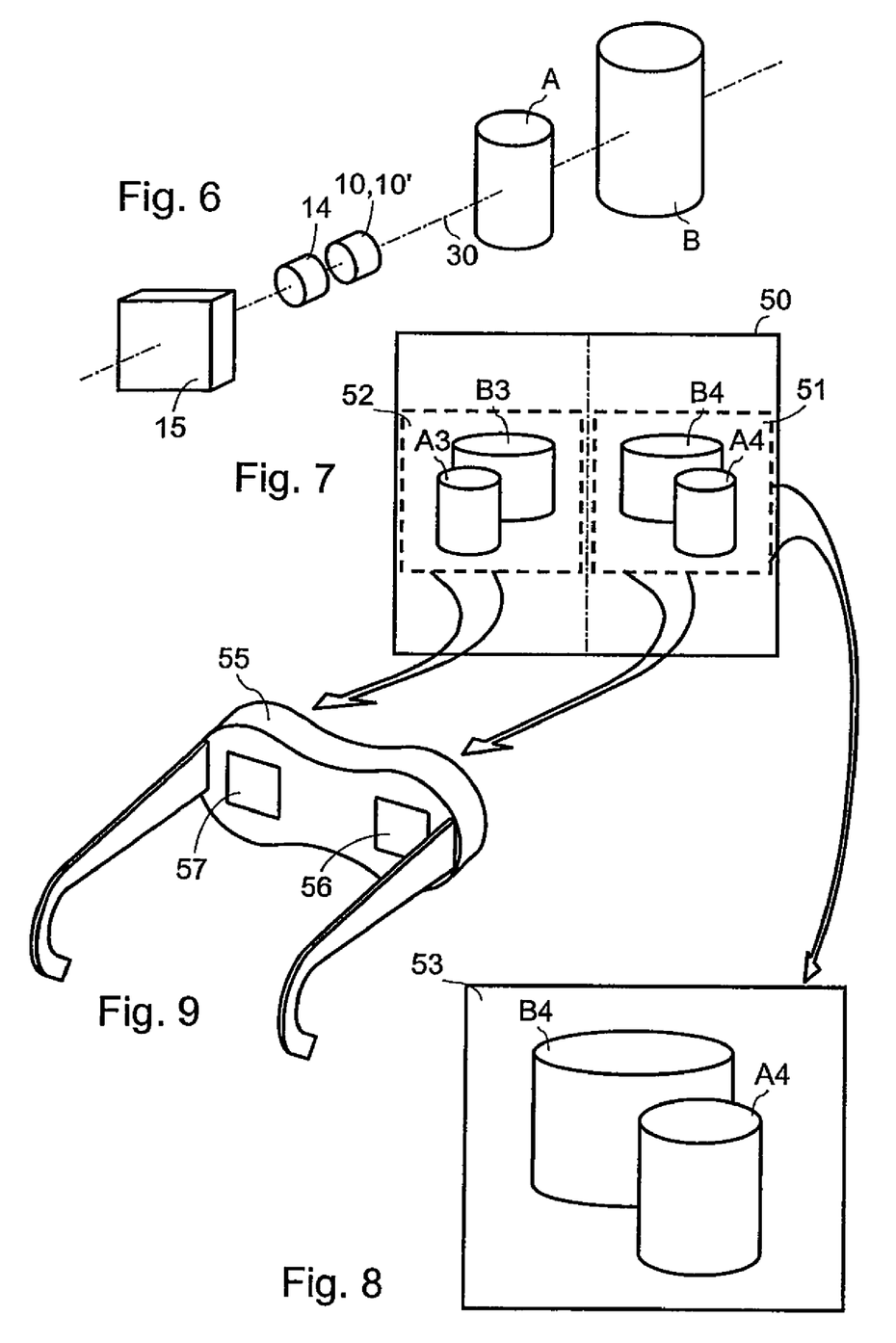
FIG. 6 schematically represents a single CCD sensor equipped with an image splitting lens according to the invention, viewing two objects aligned on the optical axis of the lens.
FIG. 7 represents a video screen on which is formed a split image generated by the CCD sensor in the conditions illustrated by FIG. 6.
FIG. 8 shows the image represented in FIG. 7, enlarged by a factor of 2.
FIG. 9 schematically represents a pair of stereo vision glasses.

FIG. 6 represents a distal opto-electronic device of a videoendoscope comprising the CCD sensor 15 and an image splitting lens comprising at least one convergent lens 14 and the image splitting optical component 10, 10', viewing a target composed in the example in the figure of two cylinders A and B aligned on the optical axis 30.

FIG. 7 represents the video screen 50 that displays the composite image generated by the sensor 15. This composite image shows in two distinct images 51, 53, the split target A3, B3 and A4, B4, observed under two different angles by the component 10, 10'. Such a screen is used to perform on the split image the various pointing necessary to the metrology calculation procedures, which allows determining, for example, the observation distances of cylinders A and B or their respective diameters.

Nevertheless, the composite structure of such a composite image is not appropriate for the simple observation of the target. To solve this problem while avoiding having to replace the optical head that integrates the image splitting lens 10 or 10', and 14, with an optical head without such a lens, the invention suggests performing during the video signal processing for generating the composite image an enlargement process with a ratio 2 applied to an image section 51 representing the observed target and occupying a quarter of the viewing surface of the video screen. The image 53 thus obtained and displayed is represented in FIG. 8. In this way, only one of the two images of the target composing the split image is displayed, for example the one on the right showing section A4, B4 of the split target.

The split images 51, 52 of the target that substantially occupy a quarter of the video screen display surface can also be simultaneously subjected to an enlargement process with a ration 2 in order to be displayed on two miniature video screens 56, 57 integrated in a pair of stereo vision glasses 55 shown in FIG. 9.

Figure 10:
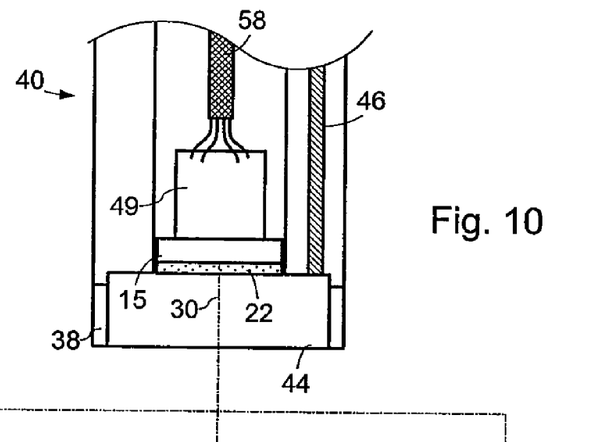
FIG. 10 schematically represents a longitudinal section of the structure of the distal part of a videoendoscopic probe that can be equipped with interchangeable distal heads.

FIG. 10 schematically illustrates the structure of a distal section 40 of a videoendoscopic probe that can be equipped with interchangeable distal heads. The distal section 40 houses on the one hand, a distal end 46 of a bundle of lighting fibers integrated into said probe, and on the other hand, a CCD sensor 15 protected by a distal transparent wall 22 and electrically connected to the video processor of the probe using an interface electronic micro circuit 49 and a multiple conductor cable 58. The distal section 40 is moreover equipped with an indexing and locking distal mechanical device for adapting interchangeable distal heads.

In the configuration illustrated in FIG. 10, the indexing and locking distal mechanical device comprises a distal cylinder tube 44 with two open longitudinal grooves 38 in the shape of a bayonet. The tube 44 houses the proximal cylindrical end of the interchangeable distal heads, this end having two lateral stubs 39 diametrically opposed (FIGS. 11 and 12), engaging, and then locking into the two longitudinal grooves 38 in the shape of a bayonet. The relative positions of said grooves and said stubs is calculated in order to ensure in a locking position the continuity of the light paths and opto-electronic paths of the videoendoscopic probe and the interchangeable distal heads.

The distal section 40 of the videoendoscopic probe illustrated as an example in FIG. 10 lacks any optical device, all the optical components attached to the CCD sensor 15 being under these conditions systematically integrated into the interchangeable distal heads. Additionally, one can imagine another organization in which the CCD sensor 15 of the videoendoscopic probe is systematically connected to a distal optical component, this organization would alleviate all the more the optical structure of the interchangeable distal heads.

Figure 11:
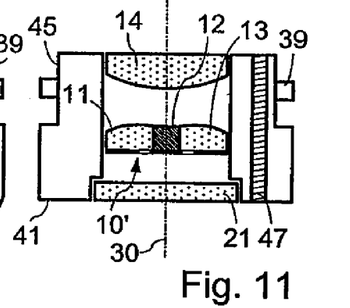
FIGS. 11 and 12 are longitudinal sections of the structure of a measurement head with distal axial and side view respectively, that integrates the image splitting optical component shown in FIGS. 3a and 3b.

FIG. 11 schematically illustrates the structure of a distal axial measurement head 41 integrating the convergent proximal lens 14 in a proximal position, the image splitting optical component 10 or 10' described in reference to FIG. 2a, 2b or 3a, 3b, and a distal transparent protection wall 21. It should be noted that the distal wall 21 could be replaced with a divergent lens ensuring the enlargement of the measurement optical field covered by the distal head 41' (see FIG. 13.)

The proximal cylinder section 45 of the distal head 41 is designed to be housed in the cylinder tube 44 constituting the distal end of the videoendoscopic probe. For this purpose, it has two external side cylinder stubs 39 that are diametrically opposed and designed to be housed in the two diametrically opposed grooves 38 in the form of a bayonet carried out in the distal cylinder tube 44. The locking system thus carried out ensures, on the one hand, the continuity of the axial bundle of lighting fibers 47 housed in the distal head 41 with the lighting fiber bundle housed in the videoendoscopic probe, and on the other hand, the correct indexing of the image splitting optical component 10, 10' with respect to the distal CCD sensor 15 of the videoendoscopic probe.

Figures 12, 14:
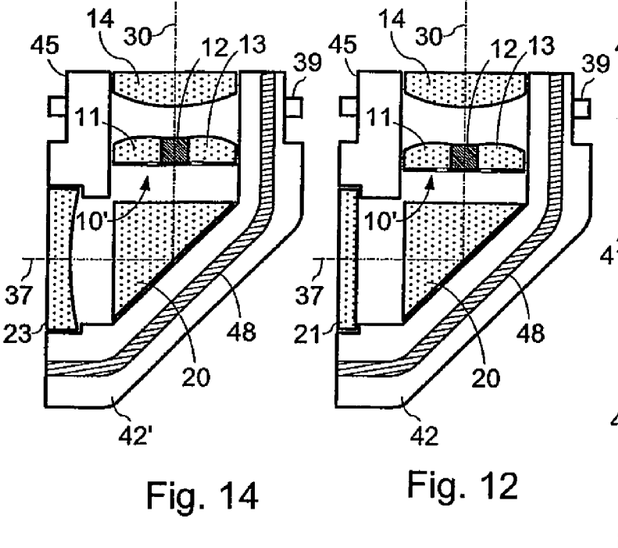
FIGS. 13 and 14 are longitudinal sections of variants of the distal measurement heads represented respectively in FIGS. 11 and 12.

FIG. 12 schematically illustrates the structure of a side measurement distal head 42. This head integrates an optical system comprising successively a convergent proximal lens 14, the image splitting optical component 10 or 10' described with reference to FIG. 2a, 2b or 3a, 3b, a deviator prism 20, and a distal transparent protection wall 21.

Figure 13:
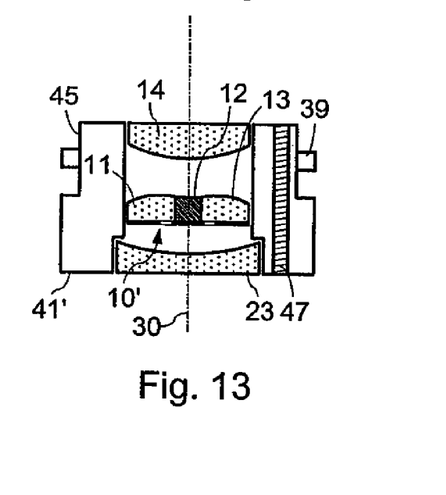

As before, the distal wall 21 can be replaced with a divergent lens 23 that ensures the enlargement of the optical measurement field covered by the distal head 42' (see FIG. 13).

The locking system of the distal head 42 on the videoendoscopic probe to which it is attached is identical to the one described above with reference to FIG. 11, in order to also ensure the continuity of the side bundle of lighting fibers 48 housed in the distal head 42 with the bundle of lighting fibers 46 housed in the videoendoscopic probe, and the correct indexing of the image splitting optical component 10, 10' with respect to the distal CCD sensor 15 of the videoendoscopic probe.

It should be noted that the image splitting device 10, 10' according to the invention ensures at the same time the function of one of the two lenses of the videoendoscope lens. This results in that the metrology optical heads 41, 42, 41', and 42' according to the invention are more compact than those of the previous art integrating an optical component that only ensures the metrology function.

Figures 15, 16, 17:
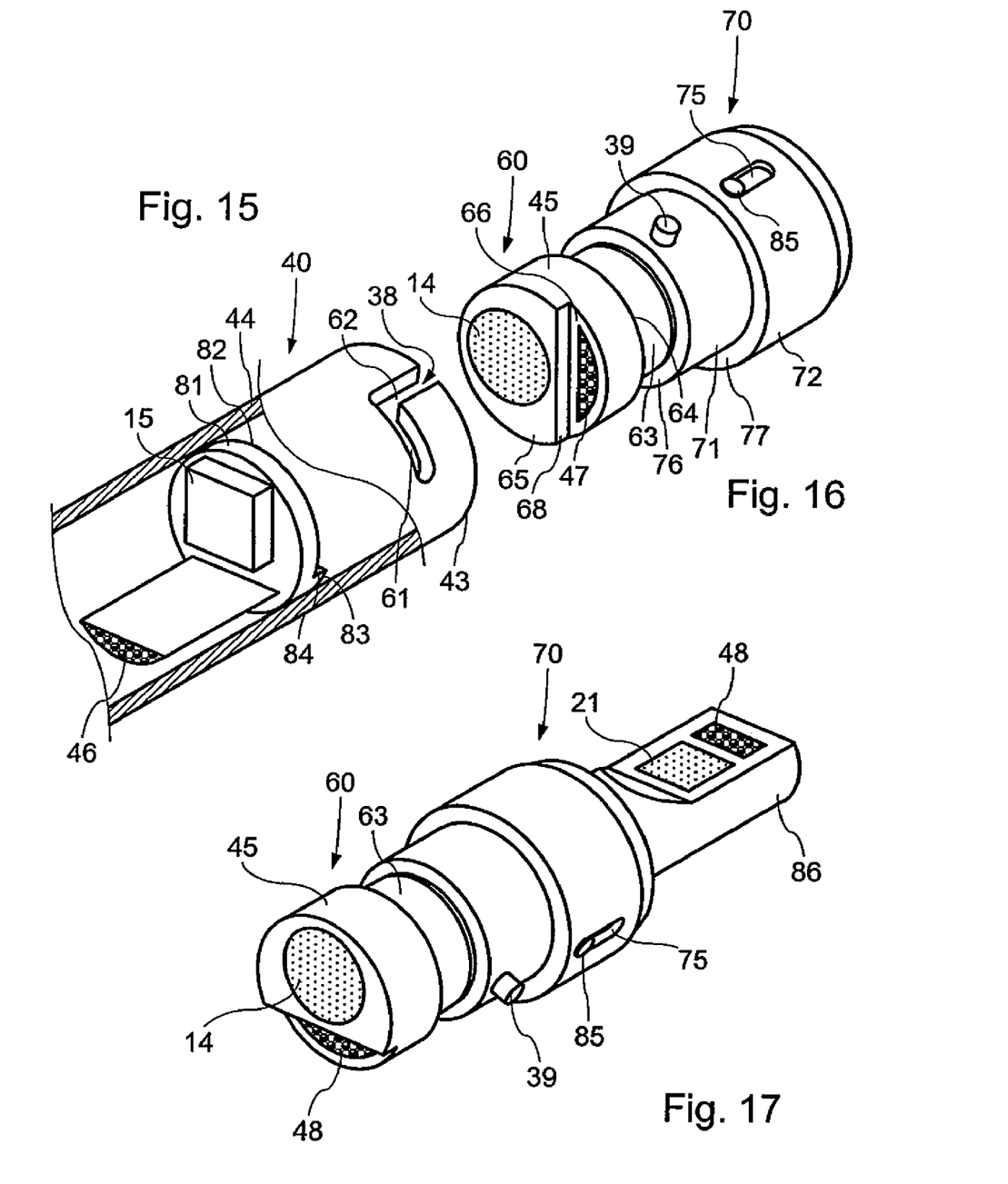
FIG. 15 represents in a more detailed and perspective view the distal end part structure of the endoscopic probe shown in FIG. 10.
FIGS. 16 and 17 represent in a more detailed and perspective view the structure of the measurement heads with distal axial view and side view shown respectively in FIGS. 11 and 12, or 13 and 14.
Figure 18:
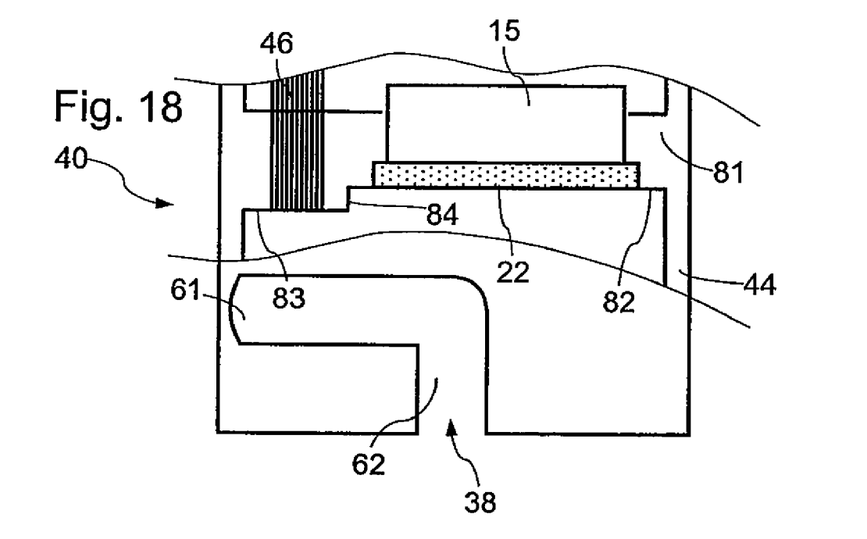
FIG. 18 is a partial longitudinal section of the distal end part structure of the endoscopic probe shown in FIG. 15.

FIGS. 15 and 18 show in greater detail the structure of the distal end part 40 of a videoendoscopic probe. This end part comprises a transversal divider 81 fixed inside the cylinder tube 44 and whose distal face 82 forms an eccentric male projection 84 with, for example, an external profile in the shape of a circle arch whose curved part merges with the internal face of the tube 44. The divider 81 has a first longitudinal hole that opens up to the distal face 82 of the divider and whose proximal section houses the CCD sensor 15, and a second eccentric longitudinal hole that opens up to the distal face 83 of the projection 84 housing the distal end of the bundle of lighting fibers 46 of the videoendoscopic probe. The distal end of the tube 44 comprises two grooves 38 in the form of bayonets that are diametrically opposed and each having an open distal section 62 that extends lengthwise and a closed transversal proximal section 61.

Figure 19:
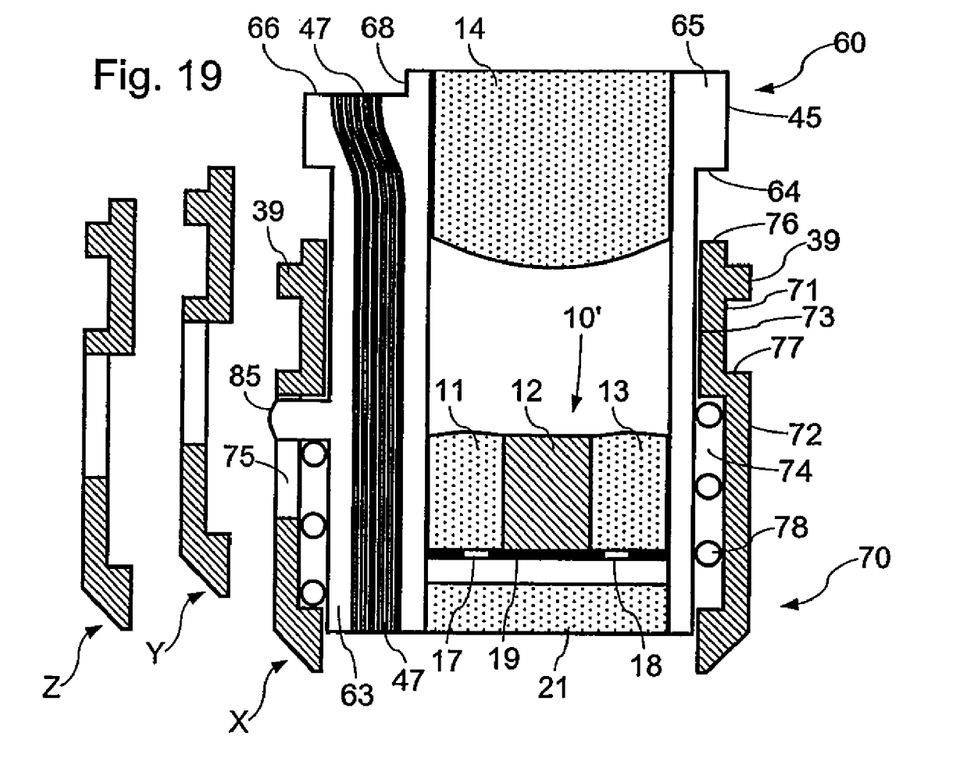
FIG. 19 is a longitudinal section of the structure of the measurement head with distal axial view, represented in FIG. 16.

FIGS. 16 and 19 show in greater detail the structure of an axial view removable head, which can be locked on the distal section 40 of the videoendoscopic probe shown in FIG. 15. This head comprises a proximal part 60 in the shape of a cylinder that houses the optical components and the lighting fiber integrated into the head, and whose distal section is wrapped in a sliding manner by a locking part 70 in the shape of a cylinder tube. The proximal part 60 has a proximal section 45 whose external diameter is compatible with the internal diameter of the tube 44 of the distal section 40, and a distal section 63 with a smaller diameter and including an external radial finger 85. The proximal 65 face of the proximal part 60 has a female recess 68 designed to house, when in a locked position, the male projection 62 located at the level of the distal face 58 of the transversal divider 57 of the distal section 40. This recess 68 has, for example, an external profile in the shape of a circle arch. The proximal part 60 comprises additionally a first longitudinal hole that opens on the proximal face 65 and houses an optical device comprising notably a proximal lens 14, and a second eccentric longitudinal hole that opens on the proximal face 66 of the recess 68 and houses the bundle of lighting fibers 47 of the removable head.

The locking part 70 whose internal longitudinal hole diameter is compatible with the external diameter of the distal section 63 of the proximal part 60, includes a proximal section 71 having an external diameter that is substantially identical to the external diameter of the proximal section 45 of the part 60 and having two external radial fingers 39, which are diametrically opposed, and a distal section 72 with an external diameter identical to the external diameter of the tube 44 of the distal section 40 and having a longitudinal groove 75 in which the external side finger 85 of the proximal part 60 is to be fitted.

A helicoidal spring 78 surrounding the distal end of the distal section 63 of the part 60 is housed in the annular volume formed for this purpose in the distal section of the locking part 70. This spring is foreseen in order to exercise longitudinal pressure on the side finger 85 integrated into the distal section 63 of the part 60, this pressure urging the finger 85 towards the proximal end of the groove 75.

Under these conditions, the adaptation of the removable distal head on the distal section 40 of the videoendoscopic probe can be performed according to the following three successive phases.

During an introduction phase X corresponding to the configuration illustrated in FIG. 16, the distal end 45 of the part 60 is inserted into the distal end of the tube 44 of the probe and until the two external radial fingers 39 integrated into the locking part 70 are engaged in the longitudinal distal sections 62 of the grooves 38.

During a subsequent compression phase Y, the operator exercises a longitudinal force on the proximal end 45 of the removable head in the tube 44. In this configuration, the proximal face 65 of the part 60 is in contact with the distal face 83 of the projection 84 that houses the bundle of lighting fibers 46 of the probe. The radial fingers 39 arrive at the level of the proximal ends of the longitudinal sections 62 of the grooves 38. The proximal end 71 of the locking part 70 is completely engaged in the distal end of the tube 44, so that the proximal face 75 is in contact with the distal face 64 of the cylinder proximal section of the part 60, and so that the proximal face 77 of the distal tube 72 of the part 70 is in contact with the distal face 43 of the tube 44. The spring 78 is compressed to a maximum so that the radial finger 85 integrated into the distal section 63 of the part 60 is positioned in the distal end of the groove 75.

During a locking phase Z, the operator turns the removable head in the distal tube 44 of the probe in a counter-clockwise direction to position the fingers 39 at the level of the closed ends of the transversal sections 62 of the grooves 38. At the end of this phase, the proximal face 65 of the proximal section 45 of the part 60 is in contact with the distal face 82 of the transversal divider 81 so that the optical axes of the CCD sensor 15 of the optical system housed in the removable head are merged. The projection 84 of the transversal divider 81 is housed in the recess 68 placed in the proximal face 65 of the distal section 45 of the part 60, so that the distal face 83 of the projection 84 is in contact with the proximal face 66 of the recess 68, and that the distal end of the bundle of lighting fibers 46 of the probe are in direct contact with the proximal end of the bundle of lighting fibers 47 of the head. The proximal end 71 of the part 70 is completely engaged in the distal end of the tube 44 so that the proximal face 77 of the distal tube 725 remains in contact with the distal face 43 of the tube 44. The spring 78 is slightly released with respect to the compression phase Y, the radial finger 85 integrated into the part 60 is positioned in the median part of the groove 75.

The locking principle described above has a high level of security because it prevents any possibility of accidental unlocking. Indeed, the unlocking of the removable head requires that the operator pushes back, using a sharp tool the finger 85 towards the distal end of the groove 75, then turns the removable head clockwise to allow disengaging the fingers 38 from the grooves 38.

It should be noted that the mechanical system composed by the interlocking of the projection 84 in the recess 68 constitutes advantageously a light trap that prevents polluting the CCD sensor 15 with parasite light beams.

FIG. 17 represents a side view removable distal head comprising the same locking device than that of the axial view head represented in FIGS. 16 and 19.

With respect to the axial view head, the side view head comprises additionally a cylinder extension 86 that integrates a distal deviation prism whose input face is positioned behind the observation window 21, and the 90 degree angle of the bundle of lighting fibers whose distal end is housed in a side light window 48.

For locking security reasons, the tube 72 forming the distal section of the part 70 can be advantageously elongated in such a way so as to completely wrap the end 86 of the distal section 63 of the part 60 and conveniently indented so as to not obstruct the side observation 21 and light 48 windows. Under these conditions, the distal end of the tube 72 can be obstructed by a transversal divider in order to integrate into it a locking spring (that replaces spring 78) between the proximal face of this divider and the distal face of the part 86.

The invention claimed is:

1. An optical objective, comprising an image splitting optical component and a proximal convergent lens arranged in a proximal position with respect to the image splitting optical component, the image splitting optical component including two portions of convergent lenses having substantially a same focal length, each lens portion being crossed by an optical axis of the convergent lens from which it is formed, and an opaque central element maintaining the two lens portions spaced apart so that optical axes of the lens portions are spaced apart, the proximal converging lens cooperating with each of the two lens portions so as to form in an image plane a single composite image.

2. The objective according to claim 1, wherein the image splitting optical component is coupled to an opaque mask with two holes forming two diaphragms that are centered respectively on the optical axes of the two lens portions.

3. The objective according to claim 1, wherein the image splitting optical component has a circular right section centered on the opaque element and having a longitudinal axis parallel to the optical axes of the lens portions.

4. The objective according to claim 1, further comprising a divergent lens placed in a distal position with respect to the image splitting optical component.

5. The objective according to claim 1, further comprising reflection means placed in a distal position with respect to the image splitting optical component, for inserting a deviation of a view angle of the image splitting optical component.

6. The objective according to claim 5, further comprising a divergent lens placed in a distal position with respect to the reflection means.

7. The objective according to claim 1, having a form of an optical head comprising fixing means for being fixed in a removable manner on a distal end part to form the composite image on the sensitive surface of a video sensor housed in the distal end part.

8. The objective according to claim 7, wherein the fixing means are of the finger type designed to cooperate with a groove in the form of a bayonet, and comprise coupling means for ensuring correct alignment of the optical axis of the optical head with the video sensor.

9. The objective according to claim 7, wherein the fixing means are formed on a locking tube which is mobile in an axial manner on the optical head between distal and proximal positions, and are brought back towards the distal position by resilient return means, the coupling means being of the type male-female and placed in such a way so as to arrive in a coupled position at the end of a locking path of the locking means under the effect of the resilient return means.

10. An image splitting optical component, comprising:
two portions of convergent lenses having substantially a same focal length, each lens portion being crossed by an optical axis of the convergent lens from which it is formed; and
an opaque central element maintaining the two lens portions spaced apart so that the optical axes of the lens portions are spaced apart.

11. The image splitting optical component according to claim 10, further comprising an opaque mask with two holes forming two diaphragms that are centered respectively on the optical axes of the two lens portions.

12. The image splitting optical component according to claim 10, comprising a circular right section centered on the opaque element and having a longitudinal axis parallel to the optical axes of the lens portions.

13. A videoendoscope, comprising:
a distal end part housing a video sensor; and
a distal objective including an image splitting optical component and a proximal convergent lens arranged in a proximal position with respect to the image splitting optical component, the image splitting optical component including two portions of convergent lenses having substantially a same focal length, each lens portion being crossed by an optical axis of the convergent lens from which it is formed, and an opaque central element maintaining the two lens portions spaced apart so that optical axes of the lens portions are spaced apart, the proximal converging lens cooperating with each of the two lens portions so as to form in an image plane a single composite image.

14. The videoendoscope according to claim 13, wherein the image splitting optical component is associated with an opaque mask with two holes forming two diaphragms that are centered respectively on the optical axes of the two lens portions.

15. The videoendoscope according to claim 13, wherein the image splitting optical component has a circular right section centered on the opaque element and having a longitudinal axis parallel to the optical axes of the lens portions.

16. The videoendoscope according to claim 13, wherein the distal objective includes a divergent lens placed in a distal position with respect to the image splitting optical component.

17. The videoendoscope according to claim 13, wherein the distal objective includes reflection means placed in a distal position with respect to the image splitting optical component, for inserting a deviation of a view angle of the image splitting optical component.

18. The videoendoscope according to claim 17, wherein the distal objective includes a divergent lens placed in a distal position with respect to the reflection means.

19. The videoendoscope according to claim 13, wherein the distal objective has a form of an optical head comprising fixing means for being fixed in a removable manner on a distal end part to form the composite image on the sensitive surface of a video sensor housed in the distal end part.

20. The videoendoscope according to claim 19, wherein the fixing means are of the finger type designed to cooperate with a groove in the form of a bayonet, and comprise coupling means for ensuring correct alignment of the optical axis of the optical head with the video sensor.

21. The videoendoscope according to claim 19, wherein the fixing means are formed on a locking tube which is mobile in an axial manner on the optical head between distal and proximal positions, and are brought back towards the distal position by resilient return means, the coupling means being of the type male-female and placed in such a way so as to arrive in a coupled position at the end of a locking path of the locking means under the effect of the resilient return means.

* * * * *